United States Patent [19]

Simon et al.

[11] Patent Number: 5,346,497
[45] Date of Patent: Sep. 13, 1994

[54] SURGICAL CUTTING HEAD WITH ASYMMETRICAL CUTTING NOTCH

[75] Inventors: Gabriel Simon; William Lee; Izuru Nose; Jean-Marie Parel, all of Miami, Fla.

[73] Assignee: The University of Miami, Miami, Fla.

[21] Appl. No.: 111,591

[22] Filed: Aug. 25, 1993

Related U.S. Application Data

[63] Continuation of Ser. No. 913,474, Jul. 15, 1992, abandoned.

[51] Int. Cl.5 .............................................. A61B 17/32
[52] U.S. Cl. .................................. 606/107; 606/167; 606/180; 604/22
[58] Field of Search .................... 604/19, 22, 27, 35; 606/1, 79, 80, 107, 159, 166, 167, 169–172, 176–180

[56] References Cited

U.S. PATENT DOCUMENTS

| | | |
|---|---|---|
| 2,492,158 | 12/1949 | LeCompte . |
| 3,732,858 | 5/1973 | Banko . |
| 3,776,238 | 12/1973 | Peyman . |
| 3,815,604 | 6/1974 | O'Malley . |
| 3,882,872 | 5/1975 | Douvas et al. ............... 606/107 |
| 3,976,077 | 8/1976 | Kerfoot . |
| 3,990,453 | 11/1976 | Douvas . |
| 3,996,935 | 12/1976 | Banko . |
| 4,014,342 | 3/1977 | Staub . |
| 4,167,944 | 9/1979 | Banko . |
| 4,320,761 | 3/1982 | Haddad . |
| 4,368,734 | 1/1983 | Banko . |
| 4,530,356 | 7/1985 | Helfgott . |
| 4,531,934 | 7/1985 | Kossovsky . |
| 4,634,420 | 1/1987 | Spinosa . |
| 4,649,918 | 3/1987 | Pegg et al. ............... 606/79 |
| 4,649,919 | 3/1987 | Thimsen et al. ............ 606/80 |
| 4,706,669 | 11/1987 | Schlegel . |
| 4,782,833 | 11/1988 | Einhorn et al. ............ 606/80 |
| 4,785,826 | 11/1988 | Ward . |
| 4,825,865 | 5/1989 | Zelman . |
| 4,869,716 | 8/1989 | Smirmaul . |
| 4,909,249 | 3/1990 | Akkas . |
| 4,986,827 | 1/1991 | Akkas . |
| 5,112,299 | 5/1992 | Pascaloff ............... 606/180 |

FOREIGN PATENT DOCUMENTS

| | | | |
|---|---|---|---|
| 0439281 | 1/1975 | U.S.S.R. ............... | 606/166 |
| 0984770 | 1/1983 | U.S.S.R. ............... | 606/169 |

Primary Examiner—Stephen C. Pellegrino
Assistant Examiner—Glenn Dawson
Attorney, Agent, or Firm—Cushman, Darby & Cushman

[57] ABSTRACT

Surgical cutting heads for use in infusion/aspiration devices for performing surgery on various parts of the body, are disclosed. These cutting heads include, a first tube, having a cutting edge formed in its proximal end and an inner space bounded by the interior surface of this tube. This first tube contains at least one asymmetrical two-sided notch for cutting tissue, which notch proceeds distally from the first tube's proximal end to an apex where the sides of the notch meet. A first side of the notch commences at the first tube's proximal end and is generally in a plane parallel to the first tube's longitudinal axis. The second side of the notch commences at the first tube's proximal end, at a point radially inwardly therefrom, and extends into the first tube's inner space. A second open tube is disposed concentrically around the first tube and has at least one projection located at its proximal end and extending radially inwardly therefrom overhanging the first tube's proximal end. The interior surface of the second tube is opposed to the exterior surface of the first tube, and the respective opposed surfaces of these tubes define a traversable inner space between the tubes.

6 Claims, 5 Drawing Sheets

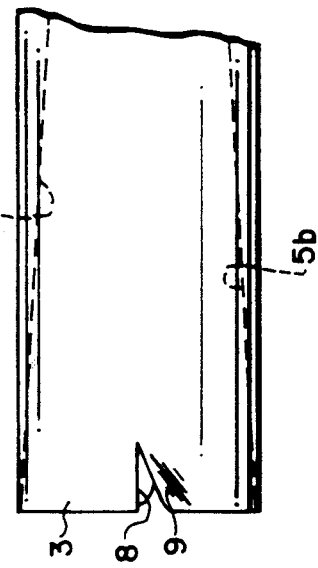
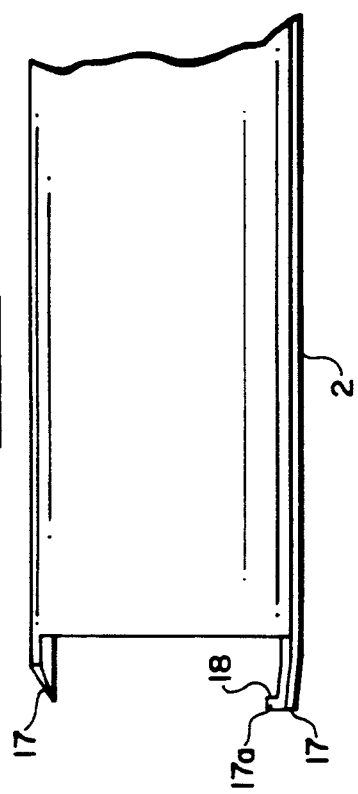
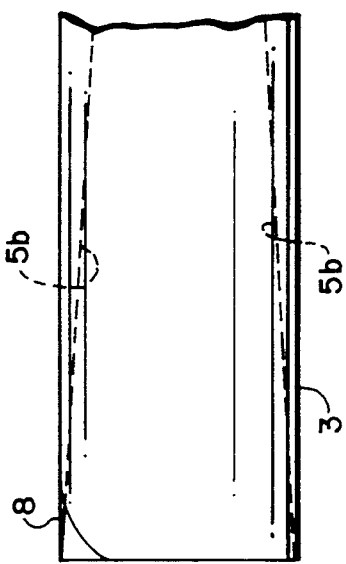
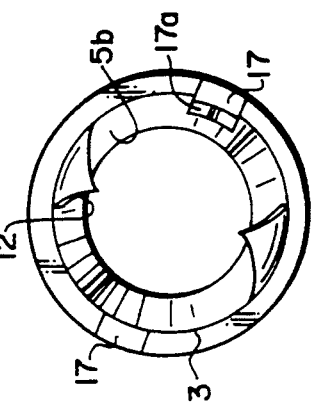

SURGICAL CUTTING HEAD WITH ASYMMETRICAL CUTTING NOTCH

This is a continuation of application No. 07/913,474, filed on Jul. 15, 1992, which was abandoned upon the filing hereof.

BACKGROUND

1. Field of the Invention

This invention relates to surgical cutting instruments. More particularly, this invention relates to novel surgical cutting heads or tips for performing surgery on various parts of the body, such as menisci (fibrous cartilages) located in body joints, e.g., knees, elbows and shoulders, or to remove malignant or nonmalignant fibroids or similar tissues through small bodily incisions from various parts of the body, and especially for use in infusion/aspiration devices for surgically removing cataractous tissue from the eye. The surgical cutting instruments of this invention will be described here with particular reference to their use in performing cataract surgery.

The eye's lens, a tough, almost completely transparent biconvex structure suspended behind the iris, is made up of an elastic capsule filled with cellular tissue. The lens adjusts the focusing of the eye when its shape is changed by the muscles of the ciliary body, to which the lens is connected by the zonular fibers.

The lens is susceptible to cataract formation—changes in the lens which make it opaque and which may hinder or destroy a person's vision depending on the cataract's size, shape and location. Cataracts can be congenital. They can also be caused by degenerative changes in the lens as a person grows older (senile cataracts). And, cataracts can result from trauma from accidents involving the eye, or from overexposure of the eye to heat, X-rays, ultraviolet rays or radioactive materials, or as a secondary effect of intraocular or systemic diseases, such as diabetes, or from exposure to various drugs. Cataracts can be cortical, involving largely or exclusively changes in the outer portion of the lens, or dense nuclear, involving primarily changes deep in the lens's interior, or can involve most if not all of the lens's proteinaceous material.

Treatments for cataracts generally involve removal of all or part of the lens through a small surgical incision (generally from about 3 to about 9 mm in length in the normal human eye, so that any instrument used during surgery can be inserted and removed without stretching the eye's tissue) made in the limbus, the portion of the sclera adjacent the cornea. Common practice has ordinarily involved then replacing the lens with a synthetic intraocular lens, or using a contact lens or a thick eyeglass to function as did the lens. Intracapsular cataract extraction ("ICCE") involves removal of the lens and the entire capsule. This technique is no longer in common use, except for subluxated lens and ocular trauma where the capsule or zonules are badly damaged. When extracapsular cataract extraction ("ECCE") is performed, a 4 to 7 mm portion of the anterior capsule and the lens's nucleus are removed, leaving the posterior capsule behind.

The main thrust of more modern cataract surgery has been towards smaller limbal incisions and less invasive approaches. Indeed, the success of the newest techniques now being developed to preserve and restore accommodation (the eye's ability to focus properly), such as refilling the entire lens with a synthetic substance once cataractous material has been removed, will depend upon the development of new instruments that can remove cataractous materials, including cataractous nuclei, through the smallest possible hole made at the periphery of the lens capsule. The present invention provides such instruments.

2. Description of the Prior Art

Cutting instruments disclosed in the prior art as being useful in cataract surgery include, inter alia, the upper and lower jaw member-containing cutting devices and rotating cutters disclosed in Banko U.S. Pat. Nos. 3,732,858 and 3,996,935, issued May 15, 1973 and Dec. 14, 1976, respectively, and the cutting devices disclosed in Hadded U.S. Pat. No. 4,320,761, issued Mar. 23, 1982, and Akkas, et al U.S. Pat. Nos. 4,909,249 and 4,986,827, issued Mar. 20, 1990 and Jan. 22, 1991, respectively.

Douvas, et al. U.S. Pat. Nos. 3,882,872 and 3,990,453, issued May 13, 1975 and Nov. 9, 1976, respectively, disclose infusion/aspiration cutting instruments useful in cataract surgery. In particular, the cutting heads or tips in the '872 patent's devices can comprise, first of all, a generally square or rectangular cutter bar fixed radially across the far end of a rotatable tube positioned inside another tube which also has a generally square or rectangular bar recessed and fixed radially across its far end; see FIG. 5 and from column 5, line 43 to column 6, line 2 of the '872 patent's specification. In another embodiment, the edge of the '872 patent's outer tube's far end can be curled inwardly to overhang the cutter bars; see FIG. 6 and column 6, lines 3–21. In a third embodiment as described in FIGS. 7 and 8 and at column 6, lines 22–45 of the '872 patent, the outer tube's far end is closed completely and the outer tube itself has a reduced bore for a distance from its proximal end so that it and the inner, rotatable tube fit closely together over that distance. The outer tube also has a pair of radial holes in proximity to its far end whose sharp edges, in conjunction with the sharp edges of an approximately 180° straight edged wall segment at the far end of the rotatable inner tube, provide cutting edges for shearing off cataractous lens material drawn through these holes. See also FIGS. 11, 14–16 and 18–25 of the '872 patent.

SUMMARY OF THE INVENTION

The novel surgical cutting heads or tips of this invention comprise:

(1) A first or inner rotatable tube which is open at its proximal end and which contains at least one asymmetrical notch which proceeds from its proximal end downwardly through the wall of the tube to an apex where the two sides of the notch meet. Each such notch has one side or edge which is generally parallel to the tube's longitudinal axis. This edge will be sharpened, preferably from the point at which it begins at the first tube's proximal end for a discernible distance along its length, i.e., part way or all the way from the proximal end to the apex of the notch. The notch's straight edge will thus serve as a cutting edge, when the first tube is rotated, oscillated or vibrated, to shear off or abrade cataractous lens material drawn into contact with it. The other side of the notch proceeds downwardly at an angle towards the apex, giving the notch generally the shape of a curved right angle triangle. The outward portion of this other side of the notch, i.e., the outer portion of the tube remaining on this side of the notch after the notch has been formed, extends inwardly for a discernible distance into the interior, fluid-traversable space defined by the tube to form an inwardly facing cutting edge, preferably doing so over the entire length of this outer portion extending from the proximal end of the tube to the apex of the notch. This inwardly facing cutting edge will also be sharpened, preferably from the point at which it begins at the first tube's proximal end for a discernible distance along its length, i.e., part way or all the way from the proximal end to the apex of the notch. If a surgical cutting head or tip of this invention is used to perform cataract surgery the notch's angled edge will thus serve, when the first tube is rotated, oscillated or vibrated, to further fragment relatively large pieces of cataractous lens material (or other materials removed from other parts of the body when surgical procedures other than cataract surgery are performed using these cutting heads or tips) which have been removed by the notch's straight edge and are being aspirated through the interior of the first tube. Alternatively, a notch or notches can first be cut in the tube and the angled side can then be provided with a separately formed and inwardly facing cutting edge having a cutting surface. The inner tube carries out its function of first cutting, abrading or shearing away cataractous lens materials and then fragmenting relatively large pieces of such materials being aspirated through the interior of the first tube into smaller pieces by being moved, e.g., rotated in clockwise or counterclockwise fashion, oscillated, or vibrated longitudinally or horizontally, by known means contained in the remainder of the infusion/aspiration device, against the below described second or exterior tube. The inner tube will also be provided with known means contained in the remainder of the infusion/aspiration device for aspirating, through the first tube's interior space, irrigating fluid and pieces of the lens broken off by the device's cutting or abrading action during cataract surgery.

(2) A second or exterior tube which is open at its proximal end and disposed concentrically around all or only a portion of the first tube so as to have an interior surface opposed to at least part of the exterior surface of the first tube to define an interior, fluid-traversable space or passage between these tubes. Irrigating fluid can be infused through this passage and out the proximal end of the second tube onto the surgical area being operated on, using known infusion means contained in the remainder of the infusion/aspiration device.

The proximal ends of the inner and outer tubes can be generally coterminous, or the proximal end of the inner tube can be slightly recessed within the outer tube to provide the surgeon with greater control in cutting away only those portions of the lens that need to be removed, and to prevent the lens from being caught by the sharp points of the cutting edge(s) in the notch(es) formed in the inner tube's proximal end and rotated or twisted when the inner tube is caused to rotate or oscillate. Guards or overhanging portions can also be provided on the proximal end of the outer tube as a further control and safety measure.

Such cutting heads or tips can replace cutting heads hitherto used in known surgical instruments of this general type, such as the cutting heads in the infusion/aspiration instruments disclosed in the Douvas, et al. '872 patent. See especially FIGS. 1-4, 9-11, 17, 19 and 26, and the accompanying descriptive material in the '872 patent. They provide significant advantages to the thus-transformed instruments, among which is a greater ability when used in performing cataract surgery or other surgical procedures to further fragment relatively large pieces of aspirated materials into smaller pieces to reduce to a minimum blockages and frictional losses produced by such aspirated larger pieces of material in prior art devices, thus increasing the instruments' effectiveness.

It is, therefore, an object of the invention to provide improved surgical cutting instruments.

A further object of the invention is to provide improved surgical cutting instruments for removing cataractous tissue from the eye.

Another object of the invention is to provide novel surgical cutting heads for use in infusion/aspiration devices for surgically removing, inter alia, cataractous tissue from the eye.

These and other objects, as well as the nature, scope and utilization of this invention, will become readily apparent to those skilled in the art from the following description, the drawings, in which like reference numerals refer to similar parts, and the appended claims.

BRIEF DESCRIPTION OF THE DRAWINGS

FIGS. 3, 4 and 5 are side elevations of the proximal end of the cutting head of FIG. 1. In FIG. 3, the device's inner tube is retracted to show a pair of guards on the proximal end of the device's outer tube. In FIG. 5, the device's inner tube, with one asymmetrical notch, is shown rotated 90° from the view given in FIG. 4.

FIG. 6 is an end elevation of the proximal end of the cutting head of FIG. 1.

In FIG. 8, the device's inner tube, with one asymmetrical notch, is shown rotated 90° from the view given in FIG. 7, but again with the device's inner tube slightly laterally extended

DETAILED DESCRIPTION OF THE INVENTION

The invention will now be described with reference to the attached drawings.

Figure 1:
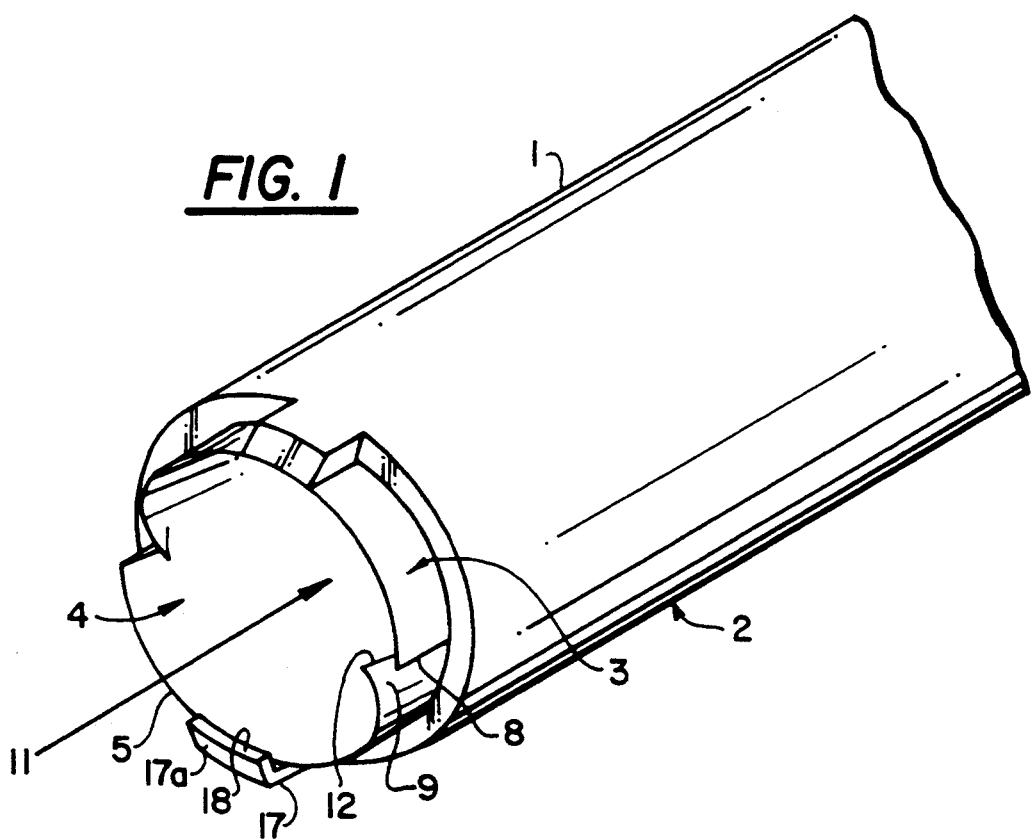
FIG. 1 is a diagrammatic perspective view of the proximal end of a cutting head of this invention.
Figure 2:
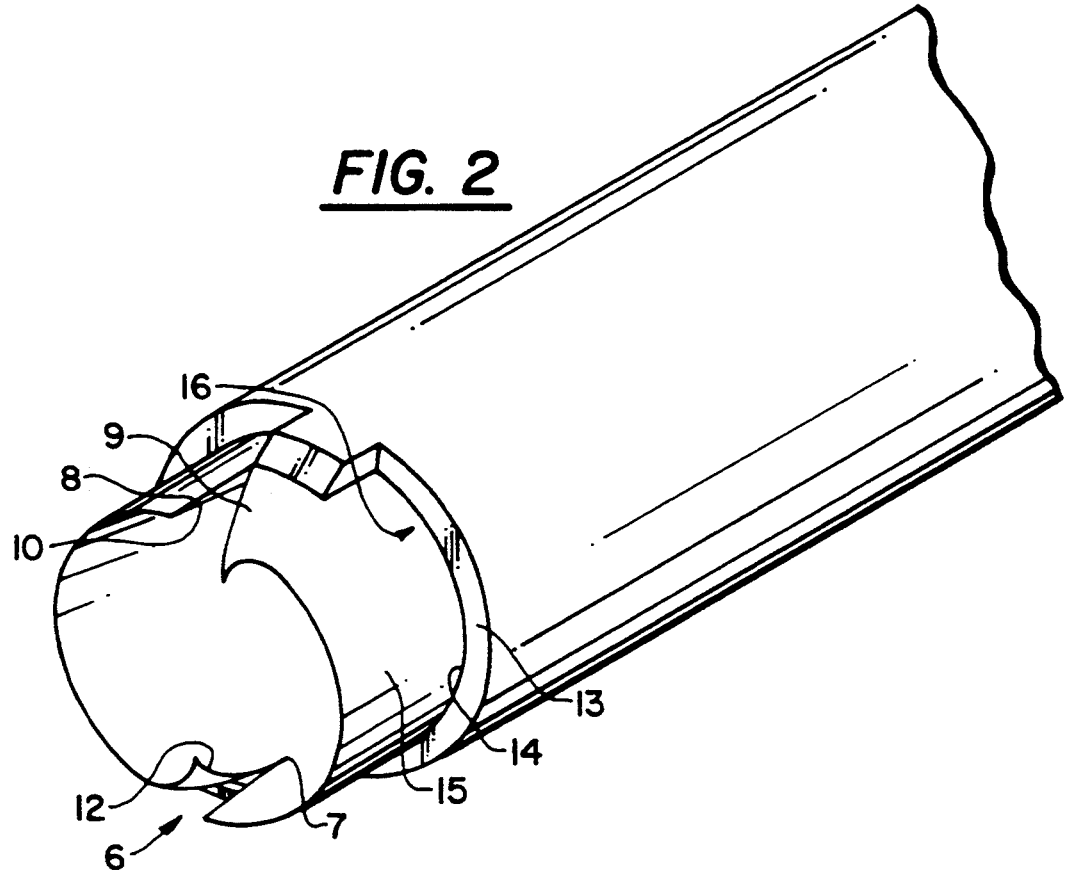
FIG. 2 is also a diagrammatic perspective view of the proximal end of the cutting head of FIG. 1, but with the device's inner tube slightly laterally extended.
Figure 7:
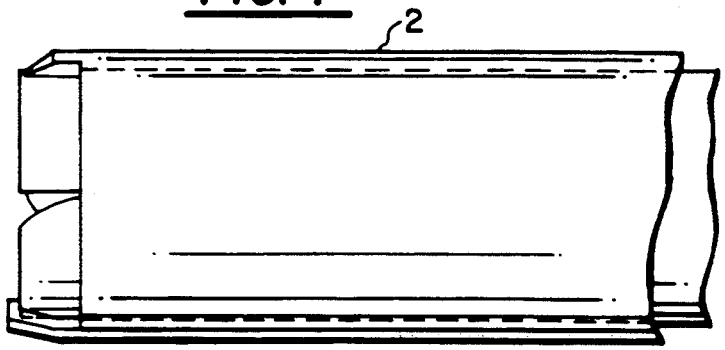
FIGS. 7 and 8 also are side elevations of the proximal end of the cutting head of FIG. 1, with portions of the device's inner tube shown in phantom for clarity.
Figure 8:
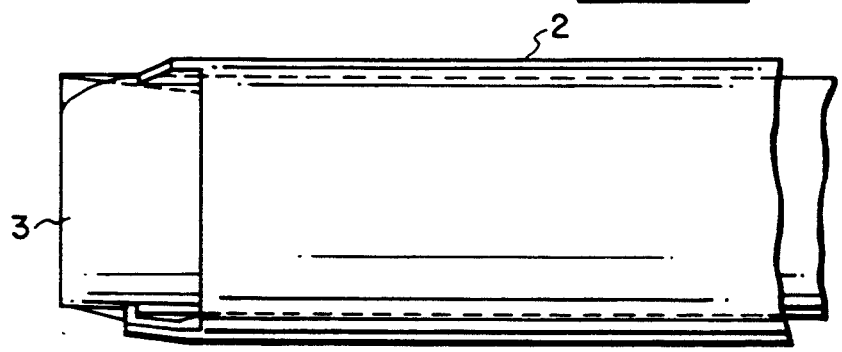
Figure 9:
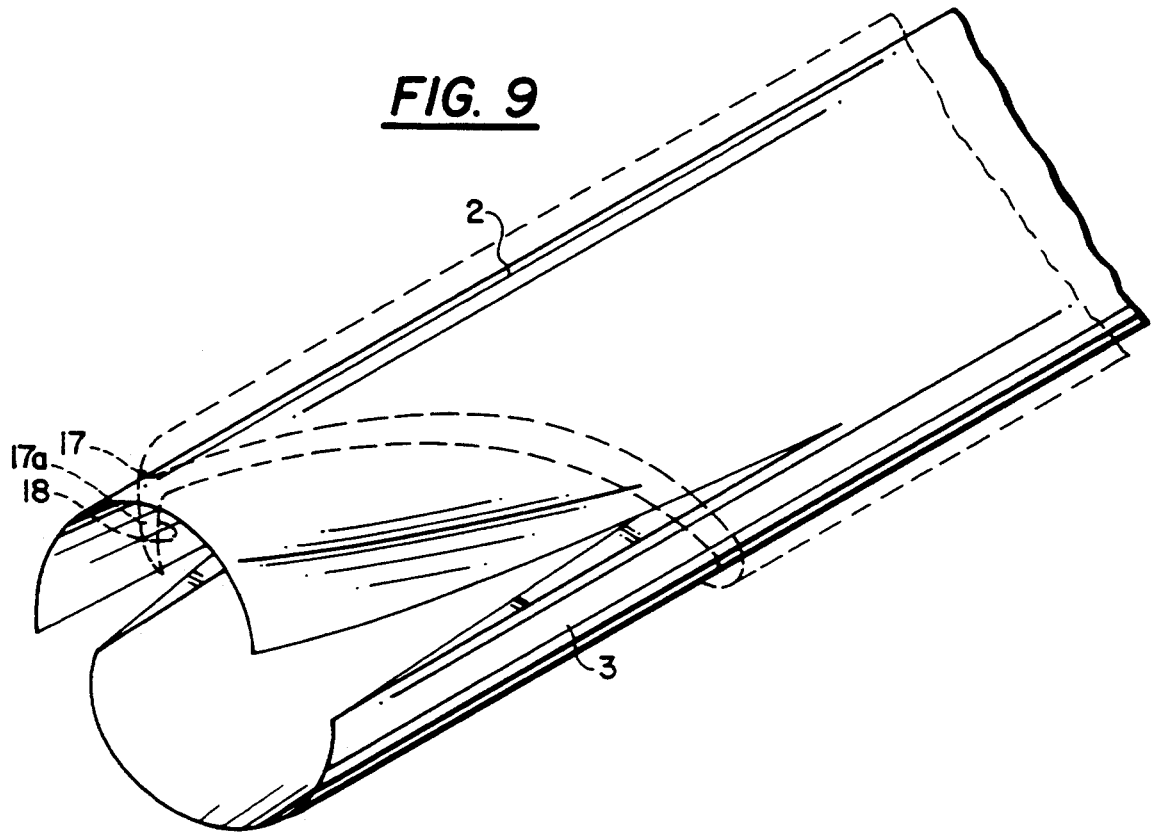
FIG. 9 is a diagrammatic perspective view of the proximal end of another embodiment of a cutting head of this invention, with the configuration of this device's outer tube shown in phantom for clarity.
Figure 10:
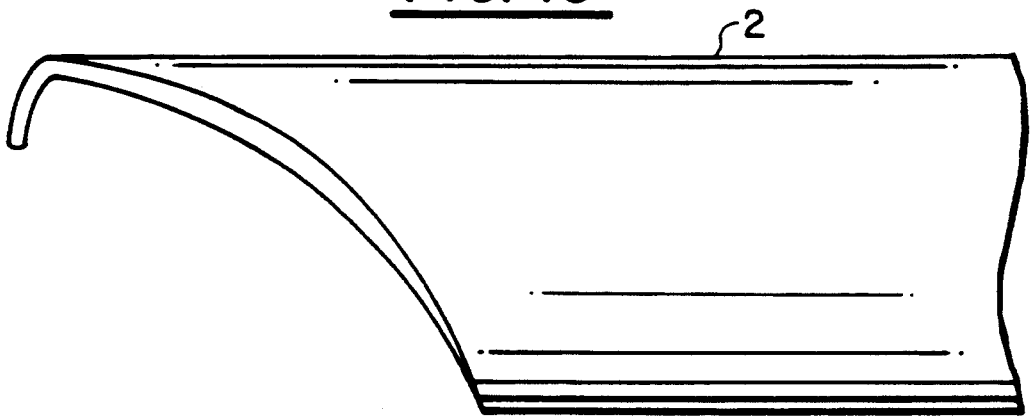
FIGS. 10, 11, 12, 14 and 15 are side elevations of the proximal end of the cutting head of FIG. 9, showing varying degrees of rotation of the device's inner tube, and with the configuration of this device's outer tube shown in phantom for clarity in FIGS. 14 and 15.
Figure 11:
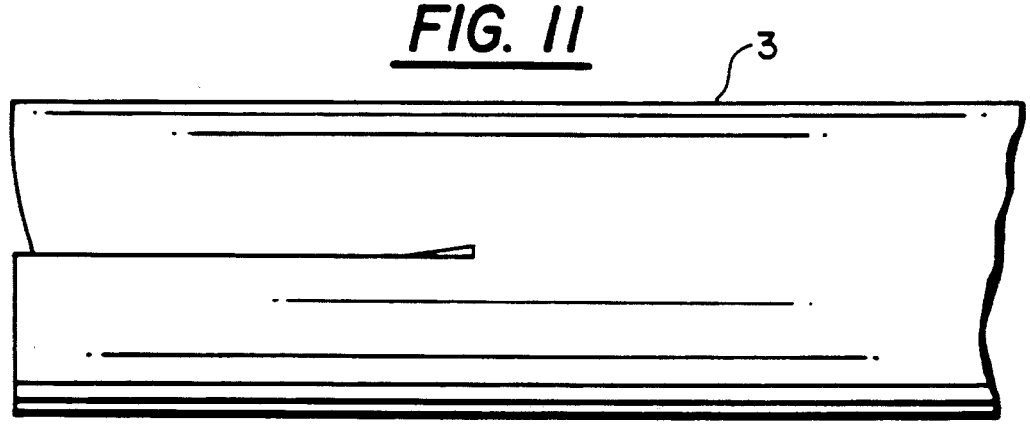
Figure 12:
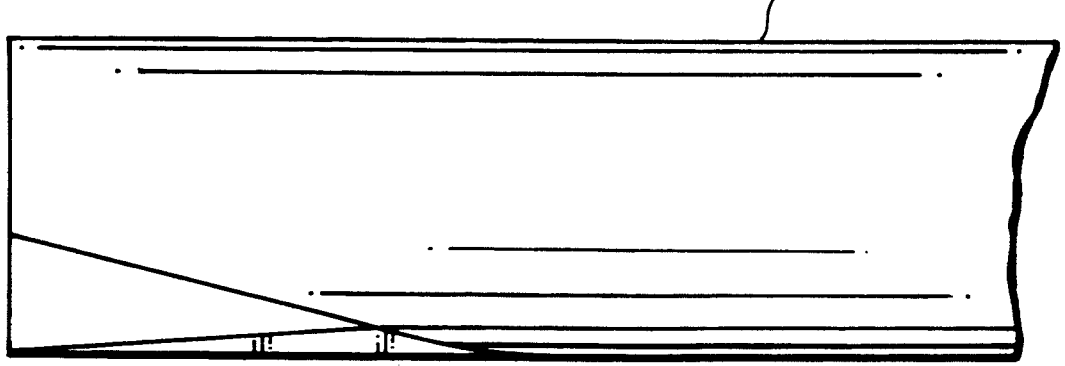
Figure 13:
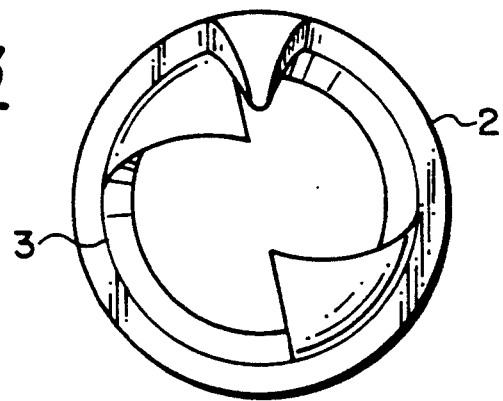
FIG. 13 is an end elevation of the proximal end of the cutting head of FIG. 9.
Figure 14:
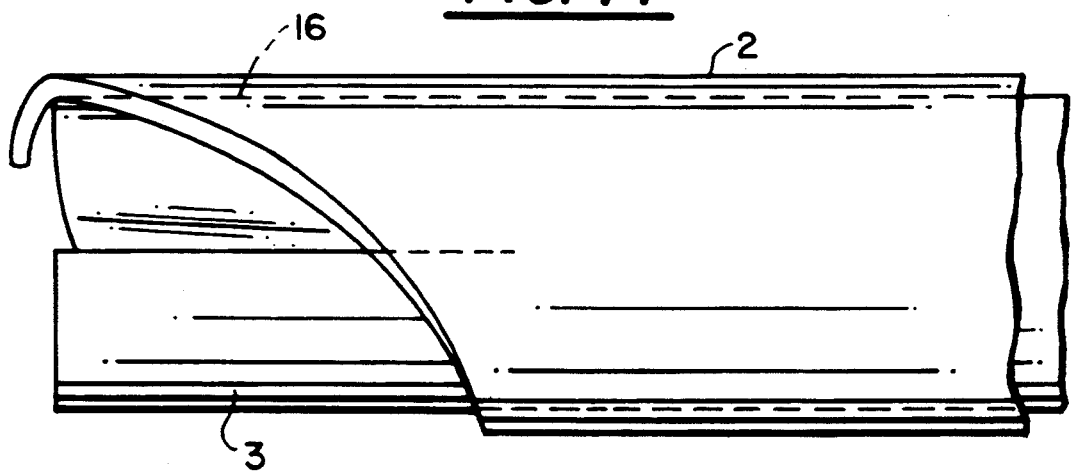
Figure 15:
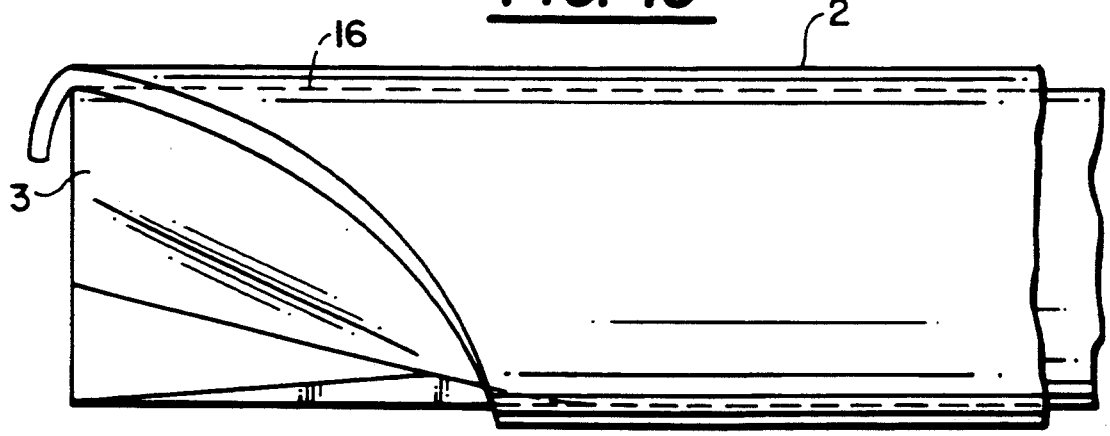

As shown in FIGS. 1-15, a surgical cutting head or tip 1 made in accordance with this invention comprises two concentric tubes 2 and 3, the former (tube 2) disposed around the latter. A first or inner movable, preferably rotatable tube 3, open at its proximal end 4, contains on its proximal end sharp cutting edges 5. The inner surface 5a of the inner tube 3 can be inwardly beveled towards its proximal end to provide the sharp cutting edges 5. Such beveling 5b is shown, for example, in FIG. 4 The first inner tube 3 also contains at least one asymmetrical two-sided notch 6, and preferably two such notches, which proceeds downwardly from the proximal end 4 of the tube 3 to an apex 7 at which the sides or edges 8 and 9 of the notch 6 meet. A first side 8 of the notch 6 is generally parallel to the longitudinal axis of the tube 3. The edge 10 of this first side 8 of the notch 6 will be formed as a sharp cutting edge, preferably although not necessarily extending from the first or inner tube's proximal end 4 to the apex 7 of the notch 6. A second side 9 of the notch 6 proceeds downwardly from the proximal end 4 of the tube 3 at an angle to meet the first side 8 at the apex 7, giving the notch 6, as shown particularly in FIG. 2, the shape generally of a curved right angle triangle. In FIGS. 2 and 8, the inner tube 3 is shown extended substantially beyond the proximal end of the outer tube 2. This will not occur when the device is in use, but has only been done here to better illustrate the structure of this embodiment of the invention.

A portion of the second, angled side 9 of the notch 6 is bent to extend inwardly for a discernable distance, e.g., for a distance of between about 20 percent and about 30 percent of the diameter of the tube 3, into the interior, fluid traversable space 11 defined by the tube 3, preferably doing so over the entire length of the outer portion of this second, angled side 9 which extends from the proximal end 4 of the tube 3 to the apex 7 of the notch 6 as shown in FIG. 2, to form an inwardly facing, sharp edged cutting blade 12. Alternatively, the second, angled side 9 of the notch 6 can be provided with a separately formed inwardly facing sharp edged cutting blade 12, which can be affixed to the second angled side 9 to act as the cutting blade 12.

The first or inner tube 3 can be rotated clockwise or counterclockwise, oscillated, or vibrated longitudinally or horizontally by known means (not shown) contained in the remainder of the infusion/aspiration device (also not shown). And further means, also not shown and also contained in the remainder of the infusion/aspiration device, will be provided for aspirating, through the first tube's interior space 11, irrigating fluid and, e.g., pieces of the lens broken off by the device's cutting or abrading action during cataract surgery.

A second or exterior stationary tube 2 which is open at its proximal end 13 is concentrically disposed around the first or inner tube 3, and has an interior surface 14 opposed to the exterior surface 15 of the first tube 3 to define an interior, fluid-traversable space or passage 16 between the tubes 2 and 3. See particularly FIG. 7. Irrigating fluid, such as saline solution, introduced by infusion means (not shown) contained in the remainder of the infusion/aspiration device, or from any other source, can be infused onto the surgical area being operated on, through means, also not shown, such as a hole or holes in the outer tube 2, into the interior space 16 and out the proximal end 13 of the second tube. When performing cataract surgery using this device the irrigating fluid maintains the stability of the eyeball and, at the same time, carries away the pieces of lens abraded during surgery by the sharp cutting edges 10 and 12 by aspiration through the first tube's interior space 11.

The proximal ends 4 and 13 of the exterior and interior tubes 2 and 3, respectively, can be coterminous, or the proximal end 4 of the inner tube 3 can be slightly recessed within the exterior tube 2. This latter modification provides the surgeon with greater control in cutting away only those portions of the lens that need to be removed, and to prevent the sharp points of the cutting edge or edges 10 and 12 in the notch(es) formed in the inner tube's proximal end 4 from catching and rotating the lens capsule when the inner tube 3 is caused to rotate or oscillate during surgery. The exterior tube 2 can also be provided, at its proximal end 13, with one or several guards 17, e.g., two such guards, with such guards preferably being ones having a smooth outer surface 17a, as shown, e.g., in FIGS. 1, 3 and 9. Such guards can also be formed to include a portion 18 that overhangs the proximal end 4 of the inner tube 3, out of contact therewith, as shown, e.g. in FIGS. 1, 3, 7 and 9, again to provide greater control to the surgeon and greater safety for the patient. The guards 17, as shown, can have one or more edges that overhang the interior tube 3. Indeed, if desired, a guard 17 can be formed around all or a majority of the proximal end 4 of the exterior tube 2 to overhang the proximal end 13 of the interior tube 2.

The sharp edge 10 of the notch(es) 6 in the inner tube 3, when moved against the exterior stationary tube 2, cuts, abrades or shears away tissue material, e.g., cataractous lens materials, being removed by the surgeon.

By way of example, the overall length of surgical cutting heads for cataract surgery made in accordance with this invention need be no longer than the maximum diameter of the cornea plus about 2 mm, hence about 15 mm. This length should allow the cutting head to reach the entire lens. Further, because of the increased efficiency which results from decreased blockages and frictional losses in these cutting heads while aspirating removed lens materials, which in turn results from these cutting heads' ability to further fragment relatively large pieces of such lens materials during aspiration, their diameters across the proximal ends of their exterior tubes 2 need be no greater than about 2 mm. For example, when practicing the standard extracapsular cataract extraction technique ("ECCE"), these proximal ends can range from about 0.9 mm to about 2 mm in diameter. When practicing endocapsular cataract extraction techniques, involving lens refilling, or intercapsular cataract extraction, somewhat smaller holes or slits in the capsule can be made, e.g., holes ranging from about 0.9 mm to about 1 mm in diameter; hence in such cases the diameters across the proximal ends of these devices' exterior tubes 2 can even be smaller than about 2 mm. In all cases, of course, care will be taken when performing such surgical procedures to use a device sufficiently small in diameter so as not to unduly stretch the capsule wall through which the device is inserted.

The cutting heads of this invention are preferably made of metal, such as stainless steel, particularly when such devices are constructed for use in performing cataract surgery. All or selected parts of these devices, the inner tube 3 in particular, can also be made of materials such as ruby, sapphire, quartz, ceramics, or polyimide copolymers. By proper choice of the materials of construction, these devices can be made to be disposable in whole or in part, or reusable (after autoclaving or the use of ethylene oxide gas or other sterilization technique).

In use as a cataract surgical device, an infusion/aspiration device equipped with a cutting head 1 made in accordance with this invention, with irrigating fluid [which can be introduced by any suitable means, e.g., from a mandrel containing "0" rings (not shown) through holes (not shown) in the outer tube's side(s)] flowing through the inner space 16 between tubes 2 and 3 to infuse the eye, and with an aspirating vacuum of, e.g., from about 10 mm to about 700 mm Hg being applied through the first tube's inner space 11, will have its cutting head 1 inserted by the ophthalmic surgeon into a previously made small, linear incision (usually about 1 mm to about 3 mm in length) in the limbus, with care being taken not to stretch the tissue. Because the lens is somewhat deformable, the aspirating vacuum applied to the proximal end 4 of the cutting head 1 draws the lens into contact with the proximal end 4. The inner tube 3, set in motion by the surgeon, abrades the lens, to whatever extent desired, into small pieces. These pieces of lens material are flushed from the surgical field and carried by the flowing irrigating fluid into the first tube's inner space 11 under the influence of the aspirating vacuum. While passing through the inner space 11 the pieces of lens material are further fragmented by the action of the inner tube's cutting surface(s), following which they pass from the inner tube 3 with the flowing irrigating fluid for disposal via means not shown.

A series of foot switches may be supplied, if desired, to allow the surgeon to control the flow of irrigating fluid, the aspiration force and the speed and direction of rotation or oscillation or the amount of vibration of the cutting head. A foot switch may also be used to occasionally cease aspiration and reverse the infusion of irrigating fluid. This permits the cutting head 1 to be backflushed to spit out the occasional large piece of aspirated lens material that might block the entrance of the cutting head 1, and also insures that the eyeball will not collapse during the procedure. If additional irrigation or steadying of the lens is necessary during a particular procedure, a separate "helper" handle can be used by the surgeon.

The above discussion of this invention is directed primarily to preferred embodiments and practices thereof. It will be readily apparent to those skilled in the art that further changes and modifications in the actual implementation of the concepts described herein can easily be made without departing from the spirit and scope of the invention as defined by the following claims.

We claim:

1. A surgical cutting head for use in infusion/aspiration devices comprising:

(a) a hollow first tube, adapted to be movable when said cutting head is connected to an infusion/aspiration device, having a distal end and a proximal end having a cutting edge formed therein, said first tube being open and defining an exterior surface and an interior surface further defining an associated interior space suitable for transporting fluids and tissue particles therethrough, said first tube containing at least one asymmetrical two-sided notch for cutting tissue which proceeds distally from said first tube's proximal end along said first tube to an apex where said sides of said notch meet, a first side of said notch commencing at said first tube's proximal end and being generally in a plane parallel to said first tube's longitudinal axis, said first side having a sharpened cutting edge commencing at said first tube's proximal end and extending for a discernable distance towards said apex along said first side's length, the second side of said notch, commencing at said first tube's proximal end at a point radially inwardly from said first side having a sharpened cutting edge extending for a discernable distance into said first tube's associated interior space, and (b) a hollow second tube, adapted to be stationary when said cutting head is connected to an infusion/aspiration device, having a distal end and a proximal end, said second tube being disposed concentrically around said first tube and having at least one projection located at its proximal end and extending radially inwardly thereform overhanging said first tube's proximal end, said second tube being open at its proximal end and defining an exterior surface and an interior surface, said interior surface said second tube being opposed to and spaced from said exterior surface of said first tube and defining therewith an associated, fluid traversable inner space between said first and second tubes for communicating with said second tube's proximal end.

2. A surgical cutting head as described in claim 1 wherein said first tube contains two of said asymmetrical, two-sided notches.

3. A surgical cutting head as described in claim 1 wherein said first side of said notch has its sharpened cutting edge extending for a substantial distance along said first side's length.

4. A surgical cutting head as described in claim 1 wherein the first side of said notch has its sharpened cutting edge extending for substantially the entire distance form said first tube's proximal end to said apex of said notch.

5. A surgical cutting head as described in claim 1 wherein the second side of said notch extends inwardly for a distance of between about 20 percent and about 30 percent of the diameter of said first tube.

6. A surgical cutting head as described in claim 1 wherein said second tube contains two said projections.

* * * * *